United States Patent [19]

Davies et al.

[11] Patent Number: 6,013,242

[45] Date of Patent: Jan. 11, 2000

[54] TROPANE DERIVATIVES WITH SELECTIVE BINDING TO THE SEROTONIN REUPTAKE TRANSPORTERS FOR TREATMENT OF MENTAL ILLNESS AND AS INTERMEDIATES IN THE FORMATION OF IMAGING DIAGNOSTIC AGENTS FOR DEPRESSION

[75] Inventors: Huw M. L. Davies, Clarence Center, N.Y.; Norman Kong, Lincoln Park, N.J.; Steven R. Childers, Winston-Salem, N.C.

[73] Assignees: Wake Forest University, Winston-Salem, N.C.; The Research Foundation of State University of New York, Amherst, N.Y.

[21] Appl. No.: 09/006,915

[22] Filed: Jan. 13, 1998

[51] Int. Cl.[7] .................. A61K 31/435; A61K 51/04; C07D 401/14
[52] U.S. Cl. ................ 424/1.85; 424/1.37; 424/1.81; 424/1.89; 514/186; 514/304; 546/4; 546/125; 546/132
[58] Field of Search ..................... 514/186, 304; 546/125, 132, 4; 424/1.37, 1.81, 1.85, 1.89

[56] References Cited

U.S. PATENT DOCUMENTS

| 5,128,118 | 7/1992 | Carroll et al. | 424/1.1 |
|---|---|---|---|
| 5,262,428 | 11/1993 | Davies et al. | 514/304 |
| 5,288,872 | 2/1994 | Davies et al. | 546/132 |
| 5,342,949 | 8/1994 | Davies et al. | 546/124 |
| 5,369,113 | 11/1994 | Moldt et al. | 514/304 |
| 5,374,636 | 12/1994 | Moldt et al. | 514/304 |
| 5,380,848 | 1/1995 | Kuhar et al. | 546/124 |
| 5,391,744 | 2/1995 | Kozikowski | 546/23 |
| 5,439,666 | 8/1995 | Neumeyer et al. | 424/1.85 |
| 5,591,854 | 1/1997 | Davies | 546/14 |
| 5,760,055 | 6/1998 | Davies | 514/304 |

*Primary Examiner*—Joseph K. McKane
*Attorney, Agent, or Firm*—Zarley, McKee, Thomte, Voorhees & Sease

[57] ABSTRACT

Biologically active derivatives of the tropane ring system are provided which selectively bind either to the 5-HT or DA reuptake site, leading to compounds which have use for the treatment of clinical depression, attention deficit disorder, obesity and cocaine addiction.

21 Claims, No Drawings

TROPANE DERIVATIVES WITH SELECTIVE BINDING TO THE SEROTONIN REUPTAKE TRANSPORTERS FOR TREATMENT OF MENTAL ILLNESS AND AS INTERMEDIATES IN THE FORMATION OF IMAGING DIAGNOSTIC AGENTS FOR DEPRESSION

GRANT REFERENCE

This invention was made with government support under grants R01-DA-06301-02 and P50-DA06634 awarded by the National Institute on Drug Abuse. The government has certain rights in the invention. Additional support was received from Resolution Pharmaceuticals.

FIELD OF THE INVENTION

The tropane skeleton is a basic structural unit that can lead to compounds with diverse central nervous system (CNS) activity. Due to the rigid nature of the structure, the possibility exists for the preparation of highly selective compounds. This application describes the synthesis of tropane derivatives that selectively bind to the serotonin (5-HT) transporter and thus have the potential for the treatment of major depression, attention-deficit hyperactivity disorder, obesity and cocaine addiction. Furthermore, it describes the synthesis of trialkyltin and iodinated derivatives, that are useful for the preparation of radiolabeled compounds that can be used to map the 5-HT transporters and are therefore useful as diagnostic agents for depression.

BACKGROUND OF THE INVENTION

Major depression represents one of the most common mental illnesses, affecting between 5–10% of the population. The disease is characterized by extreme changes in mood which may also be associated with psychoses. It has generally been found that most antidepressant agents exert significant effects on the regulation of monoamine neurotransmitters. The tricyclic antidepressants, such as imipramine, are the most commonly used drugs for the treatment of depression. Their ability to inhibit the neuronal uptake of norepinephrine is believed to be a major factor behind their efficacy.

A number of new types of antidepressants have been developed in recent years. Two compounds that are currently marketed in the United States are trazodone and fluoxetine. Both of these compounds interact with the regulation of 5-HT. Trazodone controls the actions of 5-HT while fluoxetine is a potent and selective inhibitor of 5-HT reuptake. 3-Chloroimipramine which inhibits both 5-HT and norepinephrine reuptake has been extensively used as an antidepressant in Europe and Canada. Other compounds which are of current interest or have been examined as antidepressants include fluvoxamine, citalopram, zimeldine, sertraline, bupropion and nomifensine. All of these drugs inhibit monamine uptake mechanisms, but differ in selectivity between the dopamine, 5-HT and norepinephrine transporters.

Considerable attention has recently been directed to the condition known as attention-deficit hyperactivity disorder. Children with this condition tend to be very active physically but have great difficulty with situations requiring long periods of attention. Consequently, they tend to underachieve academically and can be very disruptive. Furthermore, these behavioral problems often persist in modified forms into adulthood. The condition appears to be associated with the effect of monoamines in the cerebral cortex, which are involved with control of attention. A number of stimulant drugs such as dextroamphetamine, methylphenidate as well as the tricyclic antidepressants, antipsychotic agents and clonidine have been used as medications to control the disorder. Many of these drugs interact with the monoamine uptake transporters.

Cocaine addiction represents a major societal problem. The development of compounds that can modify the biological actions of cocaine would be very beneficial for the treatment of cocaine addiction. Cocaine is an inhibitor of both the dopamine and serotonin transporter, and so potent and selective compounds for this transporter can modify the biological consequences of cocaine.

Development of radiopharmaceuticals for the functional brain imaging has progressed rapidly in recent years. Both position emission tomography (PET) and single photon emission computed tomography (SPECT) ligands are now successfully employed for the study of receptors of the central nerve system (CNS) including ligands for the dopamine, muscarenic, opiate and benzodiazepine receptors. In particular, a large number of dopamine transporter imaging agents based on cocaine or tropane derivatives, have been reported. Although a large number of tropane derivatives have been developed into the radiolabeled ligands for the dopamine transporters, there are very few radiolabeled ligands available for the serotonin transporters. (Kung, H. F., et al. *J. Nucl. Med.* 1994, 35, 93p.; Mathis, C. A., et al., *J. Labelled compd. Radiopharm.* 1994, 34, 905), and no radioligand is available for the serotonin transporters based on tropane derivatives.

It has previously been shown that cocaine and related compounds are potent inhibitors of dopamine reuptake and this leads to compounds with reinforcing properties. In recent years a number of new extremely potent cocaine analogs have been prepared based on the tropane structure (Abraham et al., Journal of Medicinal Chemistry 1992, 35, 141; Boja et al., European Journal of Pharmacology, 1990, 183, 329; Boja et al., European Journal of Pharmacology, 1991, 194, 133; Carroll et al., Journal of Medicinal Chemistry, 1992, 35, 969; Carroll et al., Journal of Medicinal Chemistry, 1992, 35, 1813; Carroll et al., Journal of Medicinal Chemistry, 1992, 35, 2497, Cline et al., Journal of Pharmacology and Experimental Therapeutics, 1992, 260, 1174; Cline et al., Synapse, 1992, 12, 37; Kozikowski et al., Medicinal Chemistry Research, 1991, 1, 312; Kosikowski et al., Journal of Medicinal Chemistry, 1992, 35, 4764; Lewin et al., Journal of Medicinal Chemistry, 1992, 35, 135; Madras et al., Molecular Pharmacology, 1989, 36, 518, Carroll, F. I., et al., *J. Chem. Soc., Chem. Commun.* 1993, 44–46; Carroll, F. I. et al., *J. Med. Chem.* 1995, 38, 379; Carroll, F. I. et al., *J. Med. Chem.* 1993, 36, 2886; Carroll et al. *J. Med. Chem.* 1994, 37, 2865; Meltzer, P. C., et al. *J. Med. Chem.* 1993, 36, 855–862; Carroll, F. I., et al. *J. Med. Chem.* 1995, 38, 379–388; Boja, J. W., et al. *J. Med. Chem.* 1994, 37, 1220–1223; Carroll, F. I., et al. *J. Med. Chem.* 1994, 37, 2865; Kozikowski, A. P., et al. *Biorg. Med. Chem. Lett.* 1993, 3, 1327–1332; Simoni, D. et al., *J. Med. Chem.* 1993, 36, 3975–3977; Kozikowski, A. P., et al. *J. Med. Chem.* 1995, 38, 3086–3093; Kozikowski, A. P., et al. *J. Med. Chem.* 1994, 37, 3440–3442; Meltzer, P. C. et al., *J. Med. Chem.* 1994, 37, 2001–2010; Madras, B. K., et al. *Synapse* 1996, 24, 340–348; Chen, Z., et al., *Tetrahedron Lett.* 1997, 38, 1121–1124; Kelkar, S. V. et al., *J. Med. Chem.* 1994, 37, 3875–3877; Chen, Z., et al. *J. Med. Chem.* 1996, 39, 4744–4749; Xu, L. et al. *J. Med. Chem.* 1997, 40, 858–863; Moldt et al., U.S. Pat. No. 5,369,113, issued Nov.

29, 1994; Moldt et al., U.S. Pat. No. 5,374,636, issued Dec. 20, 1994; Kozikowski, U.S. Pat. No. 5,391,744, issued Feb. 21, 1995; Kuhar, et al., U.S. Pat. No. 5,380,848, issued Jan. 10, 1995; Carroll, et al., U.S. Pat. No. 5,128,118, issued Jul. 7, 1992; Kozikowski, U.S. Pat. No. 5,268,480, issued Dec. 7, 1993). All of these compounds are based on the tropane skeleton. These compounds tend to selectively bind to the dopamine transporter and certain structural variations can lead to compounds that bind with very high selectivity to the dopamine reuptake site (Carroll et al., *J. Med. Chem.*, 1992, 35, 2497). Only a few tropane derivatives have been prepared that exhibit a preference for binding to the 5-HT transporter over the dopamine transporter (Boja, J. W., et al., *J. Med. Chem.* 1994, 37, 1220; Blough, B. E., et al., *J. Med. Chem.* 1996, 39, 4027–4035; Davies, H. M. L., et al., *J. Med. Chem.* 1996, 39, 2554; Blough, B. E. et al., *J. Med. Chem.*, 1997, 40, 3861–3864). All of these tropane derivatives are very similar to each other because they are all derived from cocaine as starting material.

In principle, the tropane skeleton is ideally suited to prepare highly selective compounds because it is a rigid structure and so derivatives will have rather limited conformational flexibility. It would therefore be very valuable if the binding selectivity of the tropane skeleton could be altered by appropriate structural changes so that analogs favoring binding to the 5-HT reuptake site could be prepared. In a previous Davies, et al. patent application filed Jan. 22, 1996, Ser. No. 08/589,820 now U.S. Pat. No. 5,760,055, and entitled Biologically Active Tropane Derivatives, which application is incorporated herein by reference, it is taught how the novel chemistry that was there developed has enabled preparation of a much wider range of tropane analogs than was previously accessible, leading to novel structures with moderate potency and improved selectivity for the 5-HT transporter (Davies, H. M. L., et al. *Eur. J. Pharmacol.* 1993, 244, 93; Davies, H. M. L. et al., *J. Med. Chem.* 1994, 37, 1262; Bennett, B. A. et al., *J. Pharmacol. Exp. Ther.* 1995, 272, 1176). The work that formed the basis of the previous incorporated by reference U.S. patent application has appeared as a published article (Davies, H. M. L. et al. *J. Med. Chem.* 1996, 39, 2554).

It has now been discovered that if the tropane system is modified, particularly at the aryl moiety as hereinafter described, compounds can be produced that are over 800 times more potent at the 5-HT transporter compared to the dopamine transporter and have much lower binding affinities to the norepinephrine than those that were described in the prior referred to U.S. Patent application (see examples 1 and 2 below). Since these tropanes (as described below) bind preferentially to the 5-HT transporter, they may preferentially block 5-UT transport, thus increasing synaptic levels of 5-HT. This should be helpful in treating diseases related to 5-HT function. Furthermore, many of the tropanes are iodinated compounds or the alkyltin precursors to the iodinated compounds. The high binding affinities and 5-HT selectivities of these iodinated compounds mean that the [I-125]-derivatives and others may be useful as diagnostic agents for the treatment of depression.

Accordingly, it is a primary objective of the present invention to provide a process for development of new tropane analogs which bind selectively to the 5-HT transporter.

Another primary objective of the present invention is to prepare a series of tropane analogs which are candidates for treatment of chronic depression.

A still further primary objective of the present invention is to prepare a series of tropane analogs which are candidates for the treatment of cocaine addiction.

Another objective of the present invention is to prepare a series of tropane analogs that are iodinated compounds or the alkyltin precursors to the iodinated compounds, whose [I123} derivatives should be 5-HT selective SPECT (single photon emission computed tomography) diagnostic agents for depression.

An even further objective of the present invention is to provide a wide range of tropane derivatives which can be systematically used and tested to determine structure-activity relationships for binding at dopamine, 5-HT and norepinephrine transporters.

The method and manner of accomplishing each of the above objectives as well as others will become apparent from the description of the invention that follows. It is understood that modifications may be made to the steps of the synthesis and to the compounds prepared without departing from the spirit and scope of the invention, as long as the compounds which are prepared selectively bind to the serotonin reuptake transporters.

SUMMARY OF THE INVENTION

Biologically active derivatives of the tropane ring system are provided which selectively bind either to the 5-HT or DA reuptake site, leading to compounds which have use for the treatment of clinical depression, attention deficit disorder, obesity and cocaine addiction.

According to one aspect of the present invention, there are provided compounds of Formula (1):

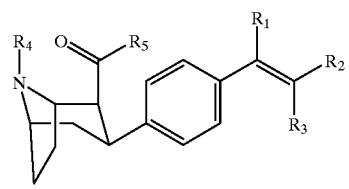

wherein $R^1$ is selected from the group consisting of hydrogen and $C_1$ to $C_8$ alkyl; $R_2$ is selected from the group consisting of hydrogen, iodo, radio isotopic halo, $C_1$ to $C_8$ alkyl, and tri lower alkyl ($C_1$ to $C_8$) tin; and $R_1$ and $R_2$ may be fused by a —N(Me)CH=CH— to form a pyrrole ring; $R_3$ is selected from the group consisting of hydrogen, iodo, or $C_1$ to $C_8$ alkyl; $R_4$ is selected from the group consisting of hydrogen and $C_1$ to $C_8$ alkyl; and $R_5$ is selected from the group consisting of hydrogen or $C_1$ to $C_8$ alkyl, and salts, solvates and hydrates thereof.

According to another aspect of the invention, there is provided a pharmaceutical composition comprising a compound of Formula (1) wherein $R_1$ through $R_5$ are as previously defined, the amount being an effective amount to bind to the 5-HT transporter, and being in conjunction with a pharmaceutically acceptable carrier.

In another of its aspects, the invention provides the use of compounds of Formula (1) as 5-HT transporter antagonists for the treatment of medical conditions mediated by 5-HT transporter stimulation.

According to another aspect of the invention, there is provided a radiopharmaceutical composition comprising a compound of Formula (1) wherein one of $R_2$ or $R_3$ is a radio halo and the other is hydrogen, $C_1$ to $C_8$ alkyl, and $R_1$ and $R_4$ and $R_5$ are as previously defined, and a pharmaceutically acceptable carrier such as a physiologically buffered saline.

In a further aspect of the invention, there is provided a method for imaging 5-HT transporters in vivo, comprising the step of administering systemically to a patient an effective amount of a radiopharmaceutical composition comprising a compound of Formula (1) wherein one of R2 or R3 is a radio halo and the other is hydrogen, $C_1$ to $C_8$ alkyl, and $R_1$ and $R_4$ and $R_5$ are as previously defined, and a pharmaceutically acceptable carrier, allowing the radiopharmaceutical to localize within the brain, and then taking an image of the brain of the patient so treated.

Compounds of the present invention are those of Formula (1) in which $R^1$ is selected from the group consisting of hydrogen and $C_1$ to $C_8$ alkyl; $R_2$ is selected from the group consisting of hydrogen, iodo, radioisotopic halo, $C_1$ to $C_8$ alkyl and tri lower alkyl ($C_1$ to $C_8$) tin; and $R_1$ and $R_2$ may be fused by a —N(Me)CH=CH— to form a pyrrole ring; $R_3$ is selected from the group consisting of hydrogen, iodo, or $C_1$ to $C_8$ alkyl; $R_4$ is selected from the group consisting of hydrogen and $C_1$ to $C_8$ alkyl; and $R_5$ is selected from the group consisting of hydrogen or $C_1$ to $C_8$ alkyl, and salts, solvates and hydrates thereof.

A preferred group of compounds of this invention are represented by Formula (1) wherein $R^1$ is selected from the group consisting of hydrogen and $C_1$ to $C_8$ alkyl, and $R^2$ or $R^3$, either one or both, are selected from hydrogen, $I^{123}$, $I^{125}$, $I^{131}$ and 18F, $R_4$ is hydrogen, and $R_5$ is alkyl. In a broader sense, $R_2$ or $R_3$ can be radioisotopic halo, tributyltin, trimethyltin, hydrogen, and/or $C_1$ to $C_8$ alkyl.

DETAILED DESCRIPTION OF THE INVENTION

In the process used to prepare 3-aryltropane derivatives are prepared by reacting 8-azabicyclo[3.2.1]oct-2-ene with an aryl Grignard reagent in the presence of catalytically effective amounts of copper (I) and/or copper (II) salts (see U.S. Pat. Nos. 5,262,428 and 5,342,949). The 3-aryl-tropane derivative starting material can be conveniently prepared by decomposing functionalized vinyldiazomethanes in the presence of certain pyrroles preferably in substantial excess of the stoichiometric amount, using a decomposition catalyst, preferably a rhodium catalyst. The catalyst may also be a copper, palladium or silver salt catalyst. This provides a bicyclic intermediate containing the basic tropane ring system which is thereafter converted to an 8-azabicyclo [3.2.1] oct-2-ene, which itself may be used as a starting material to react with an aryl Grignard reagent in providing the synthesis route to the unique tropane analogs of the present invention. The earlier referred to process U.S. Pat. Nos. 5,262,428 and 5,342,949 are incorporated herein by reference.

The focus of this application is on the composition of matter of tropane derivatives of the general formula:

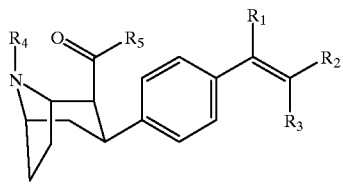

wherein $R_1$ is hydrogen or $C_1$ to $C_8$ alkyl, $R_2$ is hydrogen, iodo or $C_1$ to $C_8$ alkyl, and $R_1$ and $R_2$ may be fused by a—N(Me)CH=CH— to form a pyrrole ring, $R_3$ is hydrogen, iodo or $C_1$ to $C_8$ alkyl, $R_4$ is hydrogen or $C_1$ to $C_8$ alkyl, and $R_5$ is hydrogen, or $C_1$ to $C_8$ alkyl. The very most preferred compounds are:

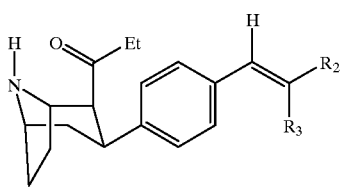

wherein either $R_1$ or $R_2$ is iodo and the other position is hydrogen or $C_1$ to $C_8$ alkyl.

The synthesis of the tropane derivatives can be achieved by the general scheme shown below. The general experimental procedure for the final synthesis step has been described in detail in U.S. Pat. No. 5,262,428. The details of the earlier process steps have been reported (Davies, et al., Journal of Organic Chemistry, 1991, 56, 5696).

The synthesis route to the basic tropane derivatives is illustrated in this series of equations shown below. The process is similar to that described in our earlier-referenced co-pending incorporated by reference application Ser. No. 08/589,520. Basically, it is the reaction of a vinyldiazomethane with a nitrogen-protected pyronyl, as illustrated in the schematic tertiary butyl pyronyl, in the presence of a rodium II catalyst. As illustrated, the rodium II catalyst is rodium octanoate. The reaction provides as its product the basic tropane skeleton. This is then selectively reduced at the 6, 7 position using a Wilkinson's catalyst. Nitrogen protecting groups are removed by acid hydrolysis using for example trifluoryl acetic acid. Conversion of the amine to N-methyl is achieved by reductive methylation using for example formaldehyde and sodium cyano borohydride. The conversion of the amine or the N-methyl to an aryl derivative (last of the three equations shown below) is achieved by copper catalyzed 1–4 addition of the appropriate Grignard reagent.

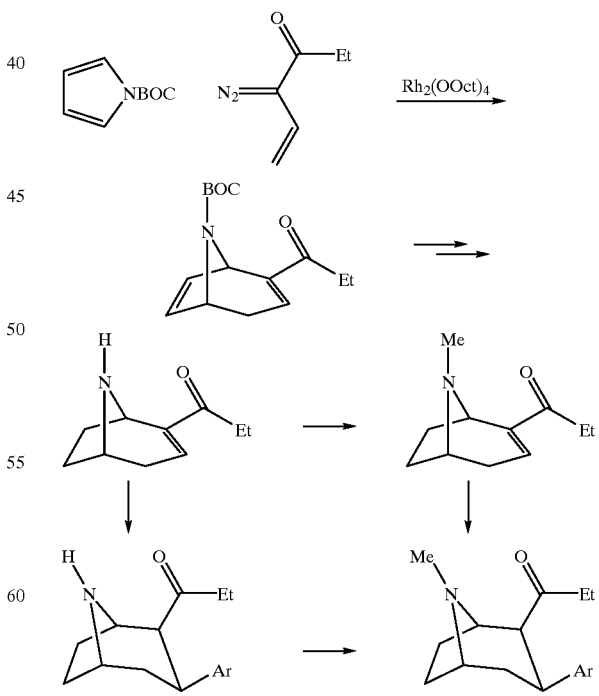

For further details on the synthesis technique, see the previously incorporated by reference pending application.

However, since the present application involves as its invention the compounds as distinct from the process of synthesis, further details of the process need not be provided herein.

The synthesis route to prepare the organotin precursors to the iodinated compounds is illustrated below and is described in conjunction with example 11 with particularity.

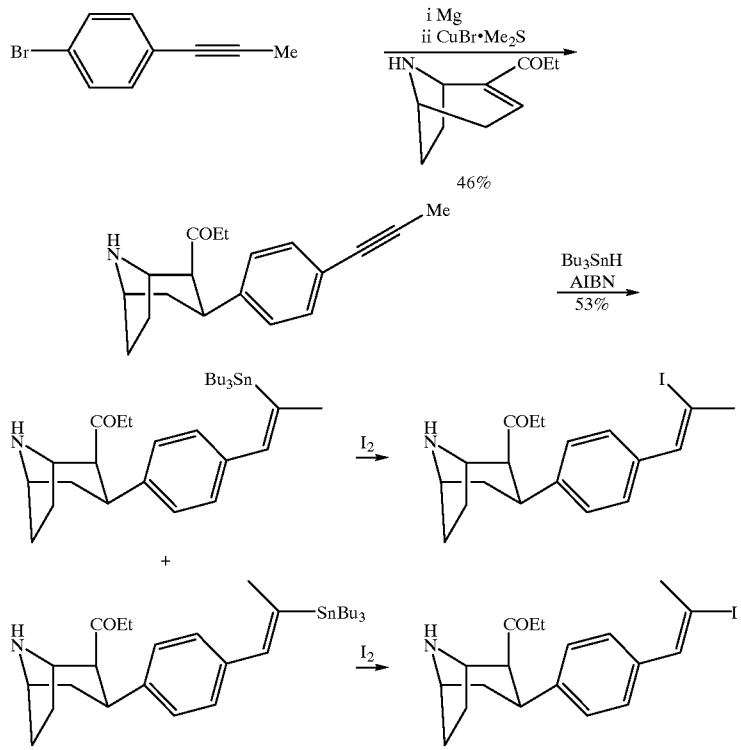

As illustrated in the above-shown equations, an aryl bromide derivative is initially converted to its Grignard reagent, using cupric-induced 1–4 addition which introduces the aryl group into the 3 position of the tropane. Radical induced addition of tributyltin hydride is initiated by azobisisobutyronitrile and results in the formation of a readily separable mixture of organotin products. The organotin products are the precursors for producing the non-radioactive iodine compounds as well as the $I^{123}$ and $I^{125}$ derivatives.

The novel tropane analogs synthesized by the vinylcarbenoid scheme listed above were tested for their ability to interact with 5-HT and dopamine transporters by displacement of radioligand binding to transporter sites. Low concentrations (10–20 pM) of $[I^{125}]$RTI-55, the potent tropane analog recently synthesized by Carroll's group (Boja et al., European Journal of Pharmacology, 1991, 184, 329), was used to label dopamine transporters in rat striatal membranes, while [$^3$H]paroxetine (Habert et al., European Journal of Pharmacology, 1985, 118, 107) was used to label 5-HT transporter sites in rat frontal cortex and [3H] nisoxetine was used to label the NE transporter sites.

In Davies, et al., U.S. Ser. No. 08/589,820, filed Jan. 22, 1996 now U.S. Pat. No. 5,760,055, which is incorporated herein by reference, the synthesis and utility of a series of novel tropanes was described. The synthesis of these compounds was based on a new synthetic method to the tropane. The p-tolyl derivative (for references on recent in vivo biological studies on this compound, see Porrino, L. J. et al., Life Sciences, 1994, 54, 511.47. (b) Hemby, S. E. et al. J. Pharmacol. Exp. Ther. 1995, 272, 1176–1186. (c) Porrino, L. J. et al. J. Pharmacol. Exp. Ther. 1995, 272, 901.), the 1-naphthyl derivative (WF30) and the 4-isopropyl phenyl derivative represent prototypical members of the class of tropanes that can be derived from this chemistry. Many compounds with binding affinity in the 1–20 nM were prepared and in general these compounds were moderately selective for the dopamine transporter. In contrast, the 2-naphthyl derivative was much more potent leading to the most potent tropane analog that has been prepared although it was unselective. However, introduction of bulky aryl substituents resulted in a compound that was quite selective for the 5-HT transporter.

The 5-HT selectivity seen of the current compounds is in sharp contrast to that of most of the previously prepared tropane analogs as these tended to be selective for the dopamine transporter. A further improvement was seen with the 4-(1-methylethenyl)phenyl derivative which was the most selective compound described in the previous case. In this current patent application, the structure is disclosed of novel tropanes that have structural elements such that further increase serotonin selectivity, and additionally, a group of iodinated derivatives that retain the serotonin selectivity, and as the radiolabeled forms, would be selective radioligands for the 5-HT transporter.

Acid addition salts of the compound of Formula 1 are most suitably formed from pharmaceutically acceptable acids, and include, for example, those formed with inorganic acids, e.g. hydrochloric, sulphuric or phosphoric acids and organic acids, e.g. succinic, maleic, acetic or fumaric acid. Other non-pharmaceutically acceptable salts, e.g. oxalates, may be used for example in the isolation of compounds of Formula 1 for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques in which an aqueous solution of the given salt is treated with a solution of base, e.g. sodium carbonate or potassium hydroxide, to liberate the free base which is then extracted into n appropriate solvent, such as ether. The free base is then separated from the aqueous portion, dried, and treated with the requisite acid to give the desired salt.

Compounds of Formula (1), wherein $R_2$ or $R_3$ are a radioisotopically labeled iodide, can be prepared by reacting compounds of Formula (1), wherein $R_2$ or $R_3$ is tri(loweralkyl)tin, with radioisotopic iodide source, for example, a solution of radioisotopically labeled sodium iodide (e.g. as a solution in 1N NaOH), in the presence of an acid and an oxidizing agent in an alcoholic solvent. Preferred conditions are Chloramine T and hydrochloric acid in ethanol.

The compounds of the invention wherein $R_2$ or $R_3$ are radioisotopic iodide are formulated as radiopharmaceutical compositions together with any physiologically and radiologically tolerable vehicle appropriate for administering the compound systemically. Included among such vehicles are phosphate buffered saline solutions, buffered for example to pH 7.4.

For use in medicine, the compounds of the present invention can be administered in a standard pharmaceutical composition. The present invention therefore provides, in a further aspect, pharmaceutical compositions comprising a pharmaceutically acceptable carrier and a Formula (1) compound or a pharmaceutically acceptable salt, solvate or hydrate thereof, in an amount effective to bind to the 5-HT transporter.

The compounds of the present invention may be administered by any convenient route, for example by oral, parenteral, buccal, sublingual, nasal, rectal or transdermal administration and the pharmaceutical compositions formulated accordingly.

Compounds of Formula (1) and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier, for example, ethanol, glycerine, non-aqueous solvent, for example, polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example, aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example, polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit doses, i.e. therapeutically effective amounts, can be determined during clinical trials designed appropriately for each of the conditions for which administration of a chosen compound is indicated and will of course vary, depending on the desired clinical endpoint. It is anticipated that dosage sizes appropriate for administering the compounds of the examples will be roughly equivalent to, or slightly less than those used currently for fluoxetine. Accordingly, each dosage unit for oral administration may contain from 1 to about 500 mgs and will be administered in a frequency appropriate for initial and maintenance treatments.

For imaging and diagnostic purposes, it is contemplated that the present compounds will be administered to patients by intravenous injection or infusion at doses suitable (e.g. between 1 and 10 mCi) to generate an image of the compound as localized within the brain, using for example a gamma camera. Preferably, the compounds will be administered and allowed to localize within the brain for 30 minutes to 48 hours prior to generating an image of the brain of the patient so treated. It is further contemplated that the method of the present invention can usefully be applied diagnose to patients suspected of suffering from depression. For these patients, diagnosis can be aided or confirmed by determining the intensity of radiolabeled compound relative to the brain of a healthy patient; lower image intensity is indicative of an underabundance of 5-HT transporter, and this is expected to be indicative of a depressed state.

The following examples are offered to further illustrate but not limit the invention.

Table 1 demonstrates the binding affinities of a series of tropanes to the dopamine (DA), serotonin (5-HT) and norepinephrine (NE) transporters (Examples 1–13). The first two compounds are the isopropenyl derivatives 1 and 2, that represent the compounds of best selectivity and potency disclosed in the previous incorporated by reference U.S. patent application. The best 5-HT/DA potency ratio was 150 and the best 5-HT/NE potency ratio was 970. Considerable improvement in selectivity was seen in many of the new compounds (3–13). The arylpyrrole derivative of example 4 is most notable with a 5-HT/DA potency ratio of 590 and a 5-HT/NE potency ratio of >25,000. The enhanced selectivity would enable these exhibit their activities cleanly at the 5-HT transporter and avoid side effects due to interactions at the other transporters. In terms of development of diagnostic agents, the iodinated compounds 11–13 are particularly relevant. The high binding affinities of these compounds makes their I-123 and I-125 analogs very interesting radioligands. In particular, the I-123 analogs are promising as SPECT agents for mapping the 5-HT transporters.

imaging agents. As a result, these imaging agents can be used to map out the serotonin receptor sites in the brain. Thus, for example, one can see a map of the serotonin receptor sites in a normal brain, and the serotonin receptor sites in a brain of a person suffering from depression, and by comparing the patterns one can predict a person needing treatment simply by looking at the image produced by the radiolabeled imaging agents of compounds 11, 12 and 13.

This invention represents the first tropane ring system compounds that are highly potent as serotonin selective uptake agents. Thus it can be seen that the invention accomplishes each of its stated objectives by the evidence summarized in Table 1.

The procedures for each of examples 3–13 are set forth below.

TABLE 1

$IC_{50}$ and $K_i$ values of tropane analogs in displacing binding of [$^{125}$I]RTI-55, [$^3$H]paroxetine and [$^3$H]nisoxetine binding in rat brain membranes[17d,23]

| Ex. | $R_1$ | $R_2$ | $R_3$ | $R_4$ | (5-HT) $K_i$ (nM) | (DA) $IC_{50}$ (nM) | (NE) $K_i$ (nM) | 5-HT/DA potency ratio | 5-HT/NE potency ratio |
|---|---|---|---|---|---|---|---|---|---|
| 1 | Me | H | H | Me | 0.82 ± 0.38 | 7.2 ± 2.1 | 794 ± 110 | 8.8 | 970 |
| 2 | Me | H | H | H | 0.11 ± 0.02 | 16 ± 4.9 | 94 ± 18 | 150 | 850 |
| 3 | —N(Me)CH=CH— | | H | Me | 25.6 ± 4.1 | 703 ± 222 | >10,000 | 24 | >15,000 |
| 4 | —N(Me)CH=CH— | | H | H | 1.05 ± 0.2 | 614 ± 98 | >10,000 | 590 | >25,000 |
| 5 | H | Me | Me | Me | 9.22 ± 2.4 | 51.3 ± 15.5 | 4134 ± 785 | 6 | 448 |
| 6 | H | Me | Me | H | 0.404 ± 0.1 | 96.3 ± 17.1 | 1251 ± 124 | 240 | 3097 |
| 7 | Et | H | H | Me | 1.13 ± 0.3 | 22.1 ± 7.76 | 1135 ± 606 | 20 | 1000 |
| 8 | Et | H | H | H | 0.194 ± 0.1 | 37.9 ± 12.9 | 347 ± 54.8 | 200 | 1790 |
| 9 | H | Me | H | Me | 1.17 ± 0.46 | 1.59 ± 0.66 | 292 ± 71.7 | 1.5 | 250 |
| 10 | H | Me | H | H | 0.236 | 1.94 ± 0.96 | 25.6 ± 9.6 | 8 | 108 |
| 11 | H | I | H | H | 0.619 ± 0.078 | 51.3 ± 5.6 | 49.7 ± 10.6 | 83 | 80 |
| 12 | H | I | Me | H | 0.566 ± 0.027 | 401 ± 73 | 365 ± 118 | 708 | 645 |
| 13 | H | Me | I | H | 0.131 ± 0.030 | 66.5 ± 11.1 | 66.7 ± 17.1 | 507 | 509 |

Table 1 summarizes each of the examples 1–13 presented. As earlier mentioned, examples 1 and 2 are representative of compounds in our previously incorporated and now patent application Ser. No. 08/589,820, filed Jan. 22, 1996, now U.S. Pat. No. 5,760,005. As can be seen in the examples illustrating the invention of the present application (examples 3–13), there is a significant improvement in 5-HT/DA potency ratio indicating that the compounds are much more receptive to the 5-HT transporter site and are therefore much better candidates for antidepressants. Most importantly as illustrated in examples 11, 12 and 13, the radiolabeled compounds, because of their high potency ratio and their radio sensitivity, can be successfully used as

EXAMPLE 3

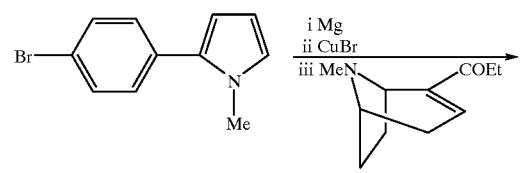

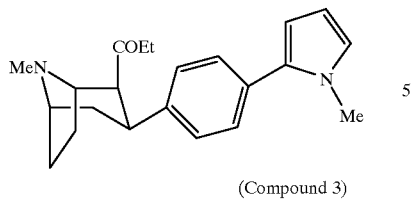

(Compound 3)                                    (Compound 4)

8-Methyl-2β-propanoyl-3β-[4-(N-methyl-2-pyrrolyl) phenyl]-8-azabicyclo[3,2,1]octane(3)

(2:1:0.1 pet ether/ether/Et₃N, 55%). ¹H NMR (400 MHz, CDCl₃) δ 7.28 (d, 2 H, J=8.8 Hz), 7.24 (d, 2 H, J=8.8 Hz), 6.68 (s, 1 H), 6.17 (m, 2 H), 3.63 (s, 3 H), 3.51 (br d, 1 H, J=6.2 Hz), 3.39 (m, 1 H), 3.09 (bs, 1 H), 2.98 (m, 1 H), 2.62 (dt, 1 H, J=2.0, 16.6 Hz), 2.40 (dq, 1 H, J=15.0, 7.5 Hz), 2.31–2.10 (m, 2 H), 2.41 (s, 3 H), 1.81–1.65 (m, 4 H), 0.75 (t, 3 H, J=7.5 Hz).

2β-Propanoyl-3β-[4-(N-methyl-2-pyrrolyl)phenyl]-8-azabicyclo[3.2.1]octane (4).

(8% Et₃N/ether, 42%) ¹H NMR (CDCl₃) δ 7.29 (d, 2 H, J=9.3 Hz), 7.17 (d, 2 H,=9.3 Hz), 6.64 (m, 1 H), 6.18 (m, 2 H), 3.72 (m, 1 H), 3.60 (s, 3 H), 3.64 (d, 1 H, J=6.8 Hz), 3.30 (dt, 1 H, J=6.9, 13.7 Hz), 2.93 (d, 1 H, J=6.9 Hz), 2.42 (dt, 1 H, J=13.7, 2.5 Hz), 2.22–1.80 (m, 3 H), 1.80–1.49 (m, 4 H), 0.66 (t, 3 H, J=6.5 Hz).

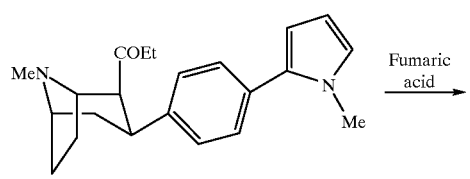
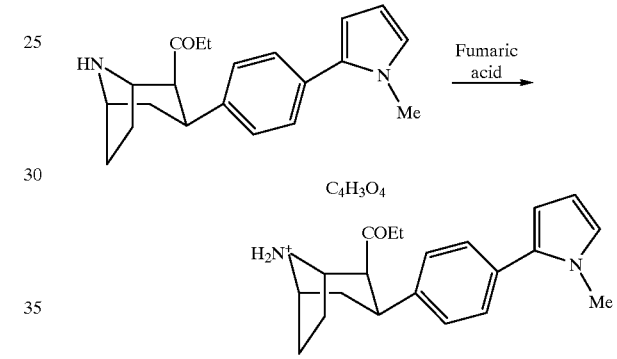

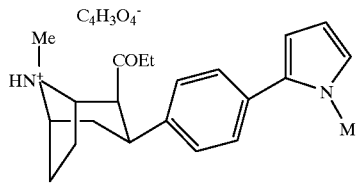

(Salt of compound 3)                          (Salt of Compound 4)

8-Methyl-2β-propanoyl-3β-[4-(N-methyl-2-pyrrolyl) phenyl]-8-azabicyclo[3,2,1]octane fumarate salt (3a).

(69%). IR (neat) 3436, 1696, 1384, 1111 cm⁻¹; ¹H NMR (300 MHz, D₂O) δ 7.19 (d, 2 H, J=8.0 Hz), 7.04 (d, 2 H, J=8.0 Hz), 6.62 (s, 1 H), 6.43 (s, 1 H), 6.00 (m, 2 H), 3.84 (m, 2 H), 3.37 (s, 3 H), 3.45–3.34 (m, 1 H), 3.23 (d, 1 H, J=5.7 Hz), 2.60 (s, 3 H), 2.54 (t, 1 H, J=14 Hz), 2.36–1.90 (m, 5 H), 1.74 (br d, 1 H, J=15 Hz), 1.20 (dq, 1 H, J=14, 7.5 Hz), 0.36 (t, 3 H, J=7.5 Hz). ¹³C NMR (75.45 MHz, D₂O/CD₃OD) δ 221.6, 172.5, 138.1, 135.9, 133.4, 129.9, 129.0, 126.1, 109.2, 65.6, 64.8, 54.1, 40.2, 40.0, 35.5, 34.5, 32.2, 25.0, 23.5, 6.8. Anal. Calcd for C₂₆H₃₂O₅N₂: C, 69.01; H, 7.13; N, 6.19. Found: C, 68.75; H, 7.14; N, 6.09.

2β-Propanoyl-3β-[4-(N-methyl-2-pyrrolyl)phenyl]-8-azabicyclo[3.2.1]octane fumarate salt.

(71% yield). IR (neat) 3422, 1692, 1609 cm⁻¹; ¹H NMR (300 MHz, D₂O) δ 7.18 (d, 2 H, J=6.4 Hz), 7.04 (d, 2 H, J=6.4 Hz), 6.64 (m, 1 H), 6.47 (s, 2 H), 5.98–6.04 (m, 2 H), 4.06 (m, 1 H), 3.98 (br d, 1 H, J=5.5 Hz), 3.37 (s, 3 H), 3.34 (m, 1 H), 2.38 (dt, 1 H, J=2.0, 13.8 Hz), 2.20–1.96 (m, 6 H), 1.68 (m, 1 H), 1.23 (dq, 1 H, J=15, 7.5Hz), 0.4 (t, 3 H, J=7.5 Hz). ¹³C NMR (75.45 MHz, D₂O/CD₃OD) δ 221.4, 172.9, 138.8, 136.0, 133.2, 129.8, 128.9, 108.4, 57.0, 55.9, 52.9, 40.3, 35.6, 35.2, 30.7, 26.7, 25.6, 24.7, 6.9. Anal. Calcd for C₂₅H₃₀O₅N₂: C, 68.47; H, 6.9; N, 6.39. Found: C, 68.75; H, 7.14; N, 6.09.

EXAMPLE 4

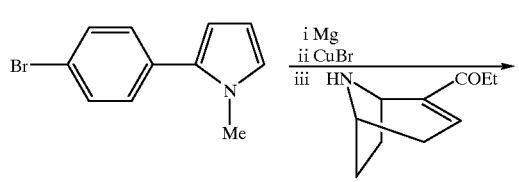

EXAMPLE 5

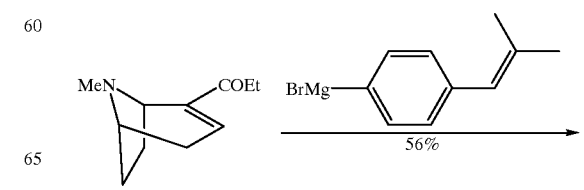

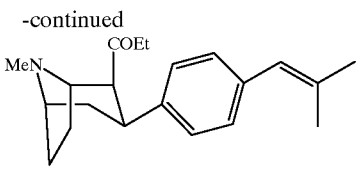

(Compound 5)

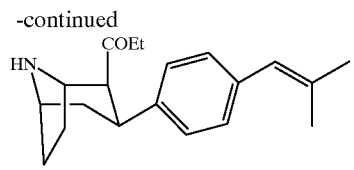

(Compound 6)

8-Methyl-2β-Propanoyl-3β-[4-(2-methylpropenyl)phenyl]-8-azabicyclo[3.2.1]octane (5)

(3:1:0.2 pet ether/ether/Et₃N, 56%). ¹H NMR (400 MHz, CDCl₃) δ 7.15 (d, 2 H, J=8.1 Hz), 7.10 (d, 2 H, J=8.1 Hz), 6.18 (s, 1 H), 3.45 (m, 1 H), 3.34 (m, 1 H), 2.93 (s, 1 H), 2.88 (m, 1 H), 2.62 (ddd, 1 H, J=12.3, 12.3, 2.3 Hz), 2.25 (q, 2 H, J=8.5 Hz), 2.19 (s, 3 H), 2.08 (m, 1 H), 1.87 (s, 3 H), 1.82 (s, 3 H), 1.72 (m, 4 H), 0.82 (t, 3 H, J=8.5 Hz).

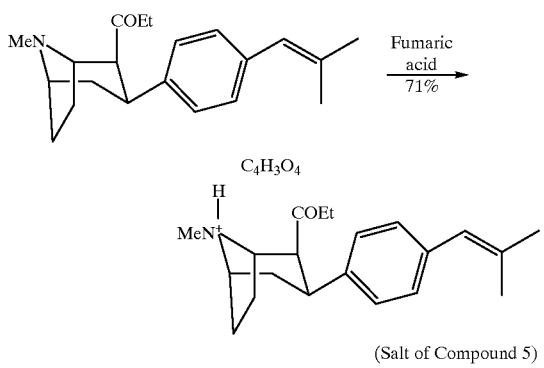

(Salt of Compound 5)

Typical procedure of the preparation of tropane salts. 8-Methyl-2β-Propanoyl-3β-[4-(2-methylpropenyl)phenyl]-8-azabicyclo[3.2.1]octane fumarate salt.

The tropane (180 mg, 0.578 mmol) was dissolved in 2-propanol (10 mL) at room temperature (warm up carefully if necessary). Fumaric acid (63.7 mg, 0.55 mmol) was added and the mixture was warmed to 50° C. until all the solids dissolved. The mixture was cooled to room temperature and the solvents were evaporated. Ether (20 mL) was added and the mixture was stirred for 2 h. The solid was collected by filtration and washed with ether (175 mg, 71%). IR (neat) 3086, 2965, 2942 1690, 1339 cm⁻¹; ¹H NMR (400 MHz, D₂O) δ 7.12 (d, 2 H, J=7.1 Hz), 7.04 (d, 2 H, J=7.1 Hz), 6.51 (s, 1 H), 6.14 (s, 1 H), 3.90 (m, 2 H), 3.44 (dt, 1 H, J=5.2, 13.7 Hz), 3.28 (d, 1 H, J=5.2 Hz), 2.64 (s, 3 H), 2.50 (t, 1 H, J=14.5 Hz), 2.36–2.16 (m, 2 H), 2.12–1.98 (m, 3 H), 1.90 (br d, 1 H, J=15.3 Hz), 1.73 (s, 3 H), 1.67 (s, 3 H), 1.25 (dq, 1 H, J=19.5, 7.5 Hz), 0.41 (t, 3 H, J=7.5 Hz). ¹³C NMR (75.5 MHz, D₂O) δ 221.1, 172.4, 138.8, 138.0, 137.1, 135.9, 130.2, 128.5, 125.2, 65.5, 64.7, 54.1, 40.1, 40.0, 34.4, 32.1, 27.3, 25.0, 23.6, 19.7, 6.9. Anal. Calcd for C₂₅H₃₃O₅N: C, 70.23; H, 7.78; N, 3.28. Found: C, 70.20; H, 7.76; N, 3.27.

EXAMPLE 6

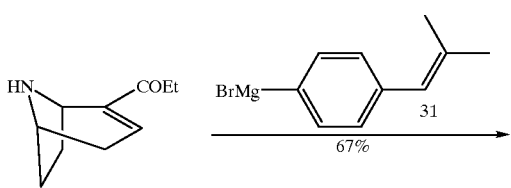

2β-Propanoyl-3β-[4-(2-methylpropenyl)phenyl]-8-azabicyclo[3.2.1]octanem (6).

(8%–15% Et₃N/Et₂O, 67%): IR (neat) 2937, 2912, 1698, 1409 cm⁻¹; ¹H NMR (400 MHz, CDCl₃) δ 7.12 (d, 2 H, J=8.0 Hz), 7.08 (d, 2 H, J=8.0 Hz), 6.20 (s, 1 H), 3.71 (m, 1 H), 3.57 (br d, 1 H, J=6.5 Hz), 3.21 (ddd, 1 H, J=12.0, 5.2, 5.2 Hz), 2.98 (br d, 1 H, J=5.2 Hz), 2.42 (dt, 1 H, J=2.0, 12.0 Hz), 2.20–1.94 (m, 3 H), 1.87 (s, 3 H), 1.82 (s, 3 H), 1.78–1.53 (m, 3 H), 0.68 (t, 3 H, J=6.5 Hz). ¹³C NMR (75.462 MHz, CDCl₃) δ 140.5, 137.6, 135.9, 129.3, 127.8, 125.3, 112.0, 56.8, 56.2, 53.9, 39.0, 36.6, 34.1, 29.4, 27.9, 27.0, 19.5, MS m/z (rel intensity) 297.3 (46), 240.2 (59), 129.1 (18), 83.1 (100), 82.1 (54), 69.2 (83), 68.2 (60), 57.2 (26), 55.1 (17). Anal. Calcd for C₂₀H₂₇ON C, 80.76; H, 9.15; N, 4.71. Found: C, 80.64; H, 9.08; N, 4.66.

EXAMPLE 7

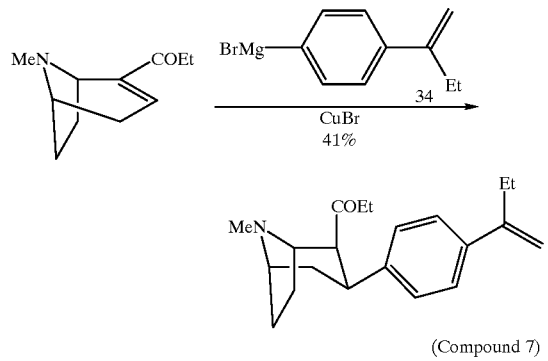

(Compound 7)

(R)-8-Methyl-2β-propanoyl-3β-[4-(1-ethylethenyl)phenyl]-8-azabicyclo[3.2.1]octanem (7)

3:1:0.2 pet ether/ether/Et₃N, 41%). IR (neat) 2960, 2935, 1714, 1353 cm⁻¹; ¹H NMR (400 Hz, CDCl₃) δ 7.31 (d, 2 H, J=7.6 Hz), 7.17 (d, 2 H, J=7.6 Hz), 5.25 (s, 1 H), 4.94 (s, 1 H), 3.50 (m, 1 H), 3.48 (br d, 1H), 2.99 (s, 1 H), 2.97 (m, 1 H), 2.60 (dt, 1 H, J=1.5, 13.3 Hz), 2.46 (q, 2 H, J=7.6 Hz), 2.42 (s, 3 H), 2.36 (dq, 1 H, J=17, 6.8 Hz), 2.30–2.05 (m, 3 H), 1.79–1.50 (m, 3H), 1.13 (t, 3 H, J=7.6 Hz), 0.68 (t, 3 H, J=6.8 Hz). ¹³C NMR (75.5 MHz, CDCl₃) δ 210.5, 149.7, 142.4, 138.8, 127.1, 125.7, 110.2, 64.7, 62.3, 59.1, 41.9, 35.1, 34.0, 33.6, 27.7, 26.3, 25.1, 12.8, 7.6. MS m/z (rel intensity) 311.3 (13), 254.3 (36), 97.3 (36), 96.2 (25), 86.0 (62), 84.0 (100), 83.0 (38), 82.0 (40), 57.1 (11). Anal. Calcd for C₂₁H₂₉ON: C, 80.98, H, 9.39; N, 4.49. Found: C, 80.96; H, 9.35; N, 4.47. [α]²⁵D=+41.5° (c 0.91, CHCl₃).

EXAMPLE 8

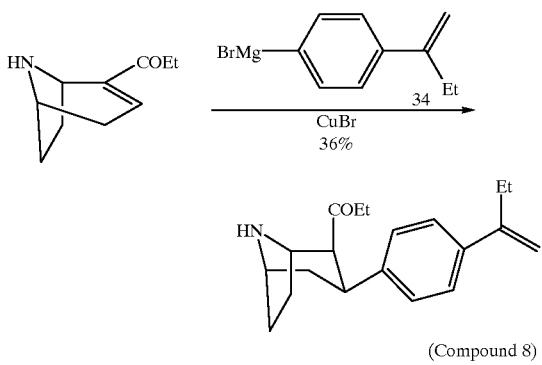

(Compound 8)

(R)-2β-Propanoyl-3β-[4-(1-ethylethenyl)phenyl]-8-azabicyclo[3.2.1]octane (8)

(1:6 Et$_3$N/ether, 36%). $^1$H NMR (400 Hz, CDCl$_3$) δ 7.31 (d, 2 H, J=8.8 Hz), 7.10 (d, 2 H, J=8.8 Hz), 5.22 (s, 1 H), 5.05 (s, 1 H), 3.74–3.69 (m, 1 H), 3.58 (br d, 1 H, J=5.2 Hz), 3.42 (dt, 1 H, J=6.0, 11.7 Hz), 2.91 (d, 1 H, J=6.0 Hz), 2.51–2.39 (m, 3 H), 2.23–1.95 (m, 4 H), 1.79–1.50 (m, 4 H), 1.08 (t, 3 H, J=6.0 Hz), 0.66 (t, 3H, J=6.6 Hz).

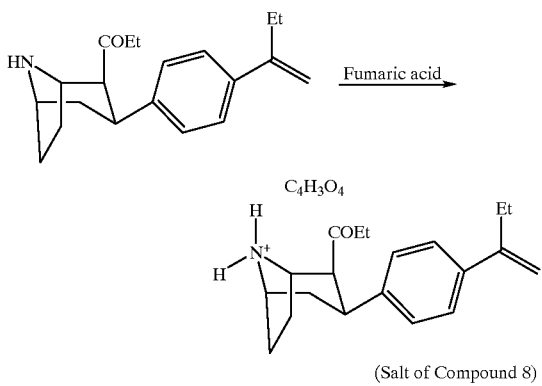

(Salt of Compound 8)

(R)-2β-Propanoyl-3β-[4-(1-ethylethenyl)phenyl]-8-azabicyclo[3.2.1]octane fumarate.

(66%). IR (neat) 3435, 3192, 1697, 1609, 1376 cm$^{-1}$; $^1$H NMR (400 Hz, D$_2$O) δ7.34 (d, 2 H, J=6.8 Hz), 7.07 (d, 2 H, J=6.8 Hz), 6.51 (s, 2 H), 5.19 (s, 1 H), 4.96 (s, 1 H), 4.10 (m, 1 H), 4.04 (m, 1 H), 3.42 (ddd, 1 H, J=12.9, 12.9, 6.2 Hz), 3.27 (d, 1 H, J=6.2 Hz), 2.44 (t, 1 H, J=12.9 Hz), 2.34 (q, 2 H, J=6.7 Hz), 2.15–1.96 (m, 6 H), 1.77 (m, 1 H), 1.28 (dq, 1 H, J=17.6, 6.8 Hz), 0.86 (t, 3 H, J=6.7 Hz), 0.40 (t, 3 H, J=6.8 Hz). $^{13}$C NMR (75.5 MHz, D$_2$O) δ 221.3, 172.6, 151.0, 141.3, 139.3, 135.9, 128.7, 127.6, 112.1, 56.9, 55.9, 52.8, 40.3, 35.1, 30.7, 28.3, 26.7, 25.5, 13.3, 6.8. Anal. Calcd for C$_{24}$H$_{31}$O$_5$N: C, 69.71; H, 7.56; N, 3.39. Found: C, 69.60; H, 7.54; N, 3.35.

EXAMPLE 9

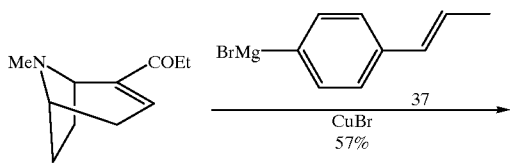

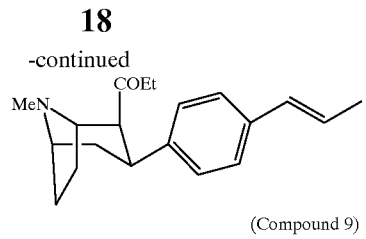

(Compound 9)

(R)-(E)-8-Methyl-2β-propanoyl-3β-[4-(1-propenyl)phenyl]-8-azabicyclo[3.2.1]octane (9).

4:1:0.2 pet ether/ether/Et$_3$N, 57%. IR (neat) 2958, 2935, 1716, 1689 CM$^{-1}$; $^1$H NMR (400 Hz, CDCl$_3$) δ 7.20 (d, 2 H, J=8.5 Hz), 7.14 (d, 2 H, J=8.5 Hz), 6.32 (d, 1 H, J=16.4 Hz), 6.15 (dq, 1 H, J=16.4, 6.9 Hz), 3.46 (m, 2 H), 3.35 (m, 1 H), 2.97 (s, 1 H), 2.92 (m, 1 H), 2.58 (dt, 1 H, J=1.7, 14.3 Hz), 2.39 (s, 3 H), 2.34 (dq, 1 H, J=17, 8.0 Hz), 2.18 (m, 1 H), 1.84 (d, 3 H, J=6.9 Hz), 1.79–1.55 (m, 4 H), 0.68 (t, 3 H, J=7.4 Hz). $^{13}$C NMR (75.5 MHz, CDCl$_3$) δ 210.6, 142.0, 135.5, 130.9, 127.4, 125.6, 124.9, 64.5, 62.4, 59.3, 42.0, 35.2, 34.1, 33.7, 26.4, 25.2, 18.4, 7.7; Anal. Calcd for C$_{20}$H$_{27}$ON: C, 80.76; H, 9.15; N, 4.71. Found: C, 80.77; H, 9.22; N, 4.67. [α]$^{25}$D=+43.0° (c 1.06, CHCl$_3$).

EXAMPLE 10

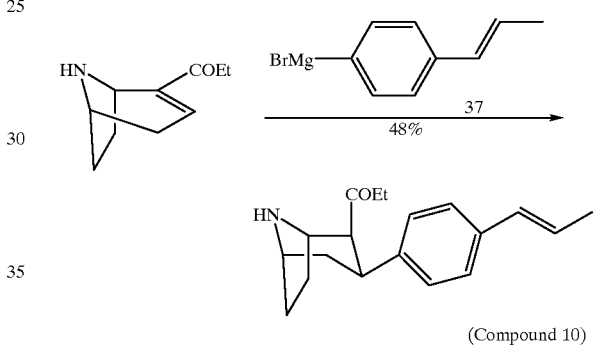

(Compound 10)

(R)-(E)-2β-Propanoyl-3β-[4-(1-propenyl)phenyl]-8-azabicyclo[3.2.1]octane (10).

(1:5 ether/Et$_3$N, 48%). $^1$H NMR (400 Hz, CDCl$_3$) δ 7.22 (d, 2 H, J=7.8 Hz), 7.06 (d, 2 H, J=7.8 Hz), 6.34 (d, 1 H, J=15.6 Hz), 6.19 (dq, 1 H, J=15.6, 6.8 Hz), 3.70 (m, 1 H), 3.56 (d, 1 H, J=7.6 Hz), 3.20 (dt, 1 H, J=13, 5.9 Hz), 2.88 (d, 1 H, J=5.9 Hz), 2.76 (br s, 1 H), 2.42 (dt, 1 H, J=1.4, 13 Hz), 2.21–1.94 (m, 2 H), 1.86(d, 3 H, J=6.8 Hz), 1.75–1.51 (m, 4 H), 0.39 (t, 3 H, J=7.6 Hz).

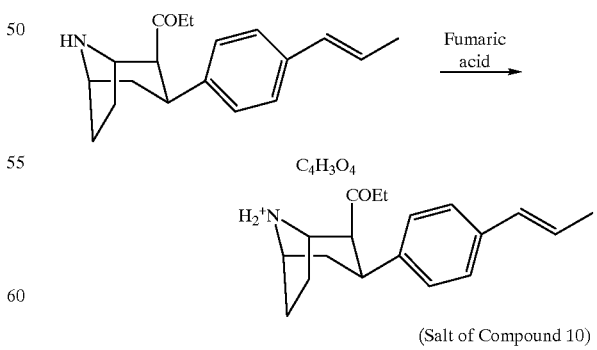

(Salt of Compound 10)

(R)-(E)-2β-Propanoyl-3β-[4-(1-propenyl)phenyl]-8-azabicyclo[3.2.1]octane fumarate salt (10a).

(73%). IR (neat) 3416, 3170, 1693, 1598, 1385 cm$^{-1}$; $^1$H NMR (400 Hz, D$_2$O) δ 7.22 (d, 2 H, J=7.5 Hz), 7.01 (d, 2

H, J=7.5 Hz), 6.28 (d, 1 H, J=16 Hz), 6.24 (d, 1 H, J=15 Hz), 6.21 (m, 1 H), 4.10 (br s, 1 H), 4.01 (br s, 1H), 3.41 (m, 1 H), 3.25 (m, 1 H), 2.42 (t, 1 H, J=14 Hz), 2.18–1.94 (m, 6 H), 1.75 (d, 1 H, J=17 Hz), 1.66 (d, 3 H, J=6.4 Hz), 1.30 (m, 1 H), 0.40 (t, 3 H, J=6.7 Hz). $^{13}C$ NMR (75.5 MHz, $D_2O/CD_3OD$) δ 220.9, 200.8, 172.3, 138.5, 138.3, 135.9, 131.0, 128.9, 128.1, 127.3, 56.9, 55.9, 52.8, 49.9, 40.3, 35.2, 30.8, 26.7, 25.6, 24.7, 18.7, 6.8. Anal. Calcd for $C_{23}H_{29}O_5N \cdot 0.2H_2O$: C, 68.53; H, 7.35; N, 3.47. Found: C, 68.45; H, 7.42; N, 3.36.

EXAMPLES 11–13

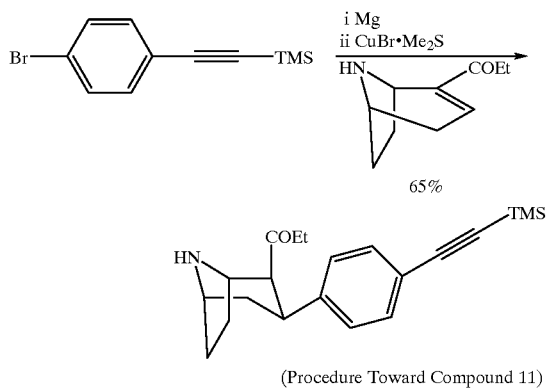

(Procedure Toward Compound 11)

Typical procedure for the conjugate addition: 2β-Propanoyl-3β-[4-(2-(trimethylsilylacetylenyl)phenyl]-8-azabicyclo[3.2.1]octane.

4-(2-(Trimethylsilylacetylenyl)phenylmagnesium bromide was generated as follows: a portion (10%) of the bromide (2.50 g, 9.64 mmol) in THF (20 mL) was added to magnesium turnings (0.262 g, 10.8 mmol). Two drops of dibromoethane was added. The reaction was initiated by heating. Once the reaction was started, the remaining bromide was added dropwise. The mixture was refluxed for 2 h after the addition and cooled to room temperature. The resulting Grignard reagent (dark brown) was added dropwise to thoroughly dried copper bromidedimethyl sulfide complex (0.300 g, 1.48 mmol). The mixture was stirred at room temperature for 15 min. and cooled to 0° C. A solution of 2-propanoyl-8-aza-bicyclic[3.2.1]oct-2-ene (0.325 g, 1.96 mmol) in THF (40 mL) was added dropwise. The ice bath was left in place and stirring was continued overnight. The solution was cooled to –78° C. and a solution of HCl (g) in dry ether (50 mL) (prepared by bubbling HCl gas into ether for 30 min.) was added in such a way that the temperature was kept below –70° C. at all times. The reaction mixture was poured into ice water (50 g) and warmed to room temperature. The organic layer was separated out (keep the aqueous layer) and washed with aqueous HCl solution (10%, 3×30 mL). The combined aqueous solution was basified with aqueous $NH_3$, saturated with sodium chloride and extracted with methylene chloride (4×60 mL). The combined extracts were dried ($MgSO_4$) and evaporated. Flash chromatography of the residue over silica gel using 10% triethylamine: 90% ether gave the tropane as a light yellow liquid (436 mg, 65%): $[\alpha]^{25}D=-95.8°$ (c 0.95, $CHCl_3$); FTIR (neat) 2955, 2154, 1697, 1408 cm$^{-1}$; $^1H$ NMR ($CDCl_3$) δ 7.36 (d, 2 H, J=8.4 Hz), 7.09 (d, 2 H, J=8.4 Hz), 3.71 (m, 1 H), 3.55 (br d, 1 H, J=5.5 Hz), 3.20 (ddd, 1 H, J=13, 5.0, 5.0 Hz), 2.89 (br d, 1 H, J=5.0 Hz), 2.42 (ddd, 1 H, J=13, 13, 2.7 Hz), 2.26–1.90 (m, 3 H), 1.78–1.62 (m, 4 H), 0.69 (t, 3 H, J=7.2 Hz), 0.23 (s, 9 H); $^{13}C$ NMR (75.45 MHz, $CDCl_3$) δ 214.7, 143.1, 132.0, 127.5, 121.1, 104.9, 93.9, 56.1, 55.6, 53.3, 38.5, 36.4, 33.4, 29.0, 27.4, 6.8, –0.2; Anal. Calcd for $C_{21}H_{29}NOSi$: C, 74.28; H, 8.61; N, 4.13. Found: C, 74.24; H, 8.67; N, 4.06.

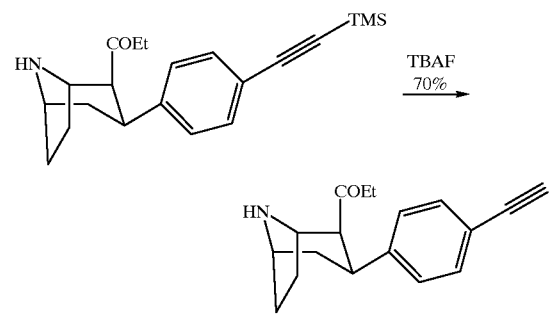

2β-Propanoyl-3β-(4-acetylenylphenyl)-8-azabicyclo[3.2.1]octane.

Tropane was dissolved in THF (20 mL) and TBAF (1.21 mL, 1.21 mmol, 1M in THF) was added dropwise at room temperature. The mixture was stirred for 2 h. Saturated aqueous $NH_4Cl$ (10 mL) was added, followed by $NH_4OH$ (10 mL). The mixture was saturated with solid NaCl and extracted with $CH_2Cl_2$ (5×20 mL). The combined organic extracts were washed with brine, dried ($MgSO_4$) and evaporated. Chromatography of the residue over silica using 10% $Et_3N$/ether gave tropane (237 mg, 81%): $[\alpha]^{25}D=-112.2°$ (c 1.05, $CHCl_3$); FTIR (neat) 2977, 2936, 1685, 1406 cm$^{-1}$; $^1H$ NMR ($CDCl_3$) δ 7.38 (d, 2 H, J=8.2 Hz), 7.11 (d, 2 H, J=8.2 Hz), 3.71 (m, 1 H), 3.57 (br d, 1 H, J=6.0 Hz), 3.20 (ddd, 1 H, J=13, 5.4, 5.4 Hz), 3.04, (s, 1 H), 2.90 (br d, 1 H, J=5.4 Hz), 2.43 (ddd, 1 H, J=13, 13, 2.9 Hz), 2.31–1.93 (m, 3 H), 1.78–1.52 (m, 4 H), 0.70 (t, 3 H, J=7.3 Hz); $^{13}C$ NMR (75.45 mHz, $CDCl_3$) δ 214.7, 143.6, 132.2, 127.7, 120.1, 110.9, 83.5, 56.2, 55.7, 53.4, 38.5, 36.4, 33.4, 29.1, 27.5, 6.9; Anal. Calcd for $C_{18}H_{21}NO$: C, 80.86; H, 7.92; N, 5.24. Found: C, 80.82; H, 7.95; N, 5.31.

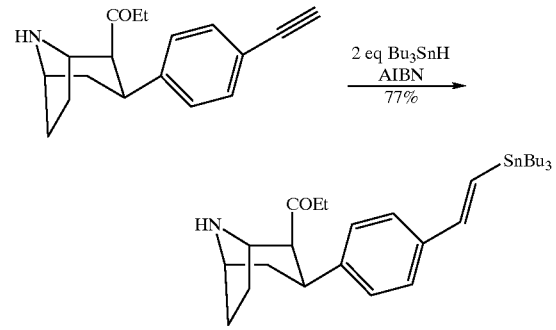

(E)-2β-Propanoyl-3β-[4-(2-tributylstannylethenyl)phenyl]-8-azabicyclo[3.2.1]octane.

Tropane (145 mg, 0.54 mmol) was dissolved in benzene (7 mL) and AIBN (10 mg, 0.06 mmol) was added. The mixture was lowered into an oil bath set at 80° C. $Bu_3SnH$ (0.29 mL, 1.08 mmol) was added in one portion. Refluxing was continued for 3 h. The solvents were removed and chromatography of the residue over silica chromatography using 5%–15% $Et_3N$/ether gave tropane (233 mg, 77%): $[\alpha]^{25}D=-69.6°$ (c 1.19, $CHCl_3$); FTIR (neat) 2955, 2922, 1704, 1460 cm$^{-1}$; $^1H$ NMR ($CDCl_3$) δ 7.31 (d, 2 H, J=8.4 Hz), 7.10 (d, 2 H, J=8.4 Hz), 6.86 (d, 1 H, J=31 Hz), 6.65 (d, 1 H, J=31 Hz), 3.75–3.68 (m, 1 H), 3.58 (br d, 1 H, J=5.9

Hz), 3.20 (ddd, 1 H, J=13, 5.1, 5.1 Hz), 2.91 (br d, 1 H, J=5.1 Hz), 2.43 (ddd, 1 H, J=13, 13, 2.2 Hz), 2.26–1.95 (m, 3 H), 1.78–1.22 (m, 18 H), 0.98–0.80 (m, 14 H), 0.70 (t, 3 H, J=7.0 Hz); $^{13}$C NMR (75.45 MHz, CDCl$_3$) δ 215.0, 145.6, 141.8, 137.01, 129.0, 127.7, 126.0, 56.3, 55.8, 53.5, 38.7, 36.3, 33.8, 29.0, 27.6, 27.2, 13.7, 9.5, 7.0; Anal. Calcd for C$_{30}$H$_{49}$NOSn: C, 64.53; H, 8.84; N, 2.51. Found: C, 64.45; H, 8.92; N, 2.56.

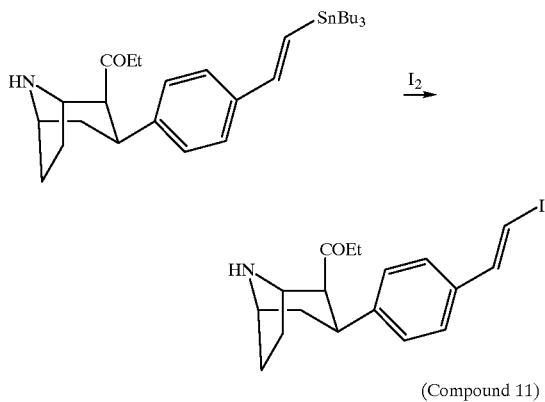

(Compound 11)

(E)-2β-Propanoyl-3β-[4-(2-iodoethenyl)phenyl]-8-azabicyclo[3.2.1]octane.

The vinyltin tropane (73 mg, 0.13 mmol) was dissolved in CH$_2$Cl$_2$ (9 mL) and argon was padded through for 10 min. Iodine (200 mg, 0.78 mmol) was added and the mixture was stirred at room temperature overnight. Aqueous Na$_2$S$_2$O$_3$ solution was then added followed by NH$_4$OH. The mixture was saturated with solid NaCl and extracted with CH$_2$Cl$_2$ (5×20). The combined organic extracts were dried (MgSO$_4$) and evaporated. Chromratography of the residue over silica using 5–15% Et$_3$N/ether gave Iodonated tropane (26 mg, 51%): [α]$^{25}$D=–71.0° (c 51, CHCl$_3$); FTIR (neat) 3328, 2970, 2937, 2914, 1693 cm$^{-1}$; $^1$H NMR (CDCl$_3$) δ 7.35 (d, 1 H, J=15.0 Hz), 7.18 (d, 2 H, J=8.0 Hz), 7.09 (d, 2 H, J=8.0 Hz), 6.76 (d, 1 H, J=15.0 Hz), 3.69 (br s, 1 H), 3.57 (br d, 1 H, J=6.2 Hz), 3.17 (ddd, 1 H, J=11.3, 5.1, 5.1 Hz), 2.89 (br d, 1 H, J=5.5 Hz), 2.80 (b s, 1 H), 2.41 (ddd, 1 H, J=11.3, 11.3, 2.7 Hz), 2.28–1.93 (m, 3 H), 1.79–1.48 (m, 4 H), 0.68 (t, 3 H, J=6.9 Hz); $^{13}$C NMR (75.45 MHz, CDCl$_3$) δ 214.7, 144.5, 142.8, 135.9, 127.9, 126.0, 76.2, 56.2, 55.7, 53.5, 38.6, 36.3, 33.6, 29.1, 27.5, 7.0; Anal. Calcd for C$_{18}$H$_{22}$NOI: C, 54.69; H, 5.61; N, 3.54. Found: C, 54.68; H, 5.66; N, 3.48.

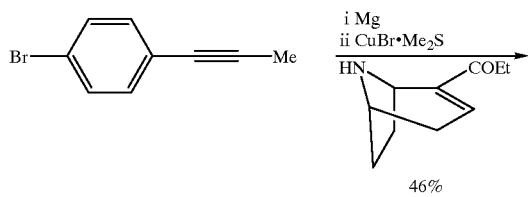

46%

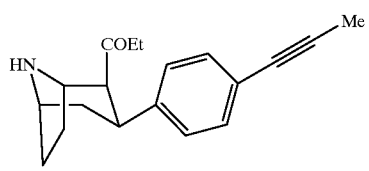

(E)-2β-Propanoyl-3β-[4-1-propynyl)phenyl]-8-azabicyclo[3.2.1]octane.

4-(Propynyl)phenylmagnesium bromide was generated as follows: A portion (10%) of the bromide (1.33 g, 6.82 mmol) in THF (15 mL) was added to magnesium turnings (0.182 g, 7.5 mmol). Two drops of dibromoethane was added. The reaction was initiated by heating. Once the reaction was started, the remaining bromide was added dropwise. The mixture was refluxed for 2 h after the addition and cooled to room temperature. The resulting Grignard reagent (dark brown) was added dropwise to thoroughly dried copper bromide-dimethyl sulfide complex (0.207 g, 1.02 mmol). The mixture was stirred at room temperature for 15 min. and cooled to 0° C. A solution of 2-propanoyl-8-aza-bicyclic [3.2.1]oct-2-ene (0.225 g, 1.36 mmol) in THF (30 Iti) was added dropwise. The ice bath was left in place and stirring was continued overnight. The solution was cooled to –78° C. and a solution of HCl (g) in dry ether (50 mL) (prepared by bubbling HCl gas into ether for 30 min.) was added in such a way that the temperature was kept below –70° C. at all times. The reaction mixture was poured into ice water (50 g) and warmed to room temperature. The organic layer was separated out (keep the aqueous layer) and washed with aqueous HCl solution (10%, 3×30 mL). The combined aqueous solution was basified with aqueous NH$_3$, saturated with sodium chloride and extracted with methylene chloride (4×60 mL). The combined extracts were dried (MgSO$_4$) and evaporated. Flash chromatography of the residue over silica gel using 5% triethylamine: 95% ether gave the tropane as a light yellow liquid (176 mg, 46%): [α]$^{25}$ D=–89.0° (c 1.02, CHCl$_3$); FTIR (neat) 3321, 2940, 2915, 1696, 1509 cm$^{-1}$; $^1$H NMR (CDCl$_3$) d 7.23 (d, 2 H, J=8.4 Hz), 7.09 (d, 2 H, J=8.4 Hz), 3.71 (m, 1 H), 3.55 (br d, 1 H, J=5.5 Hz), 3.20 (ddd, 1 H, J=13, 5.9, 5.9 Hz), 2.89 (br d, 1 H, J=5.9 Hz), 2.42 (ddd, 1 H, J=13, 13, 2.7 Hz), 2.26–1.90 (m, 3 H), 1.78–1.62 (m, 4 H), 0.69 (t, 3 H, J=7.2 Hz); $^{13}$C NMR (75.45 MHz, CDCl$_3$) δ 214.6, 141.8, 131.3, 127.3, 121.9, 85.5, 79.3, 56.0, 55.6, 53.3, 38.5, 36.3, 33.4, 29.0, 27.4, 6.8, 4.1; Anal. Calcd for C$_{19}$H$_{23}$NO.1/8 H$_2$O: C, 80.46; H, 8.26; N, 4.94. Found: C, 80.55, H, 8.14; N, 4.73.

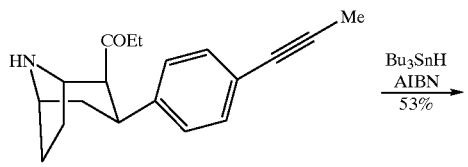
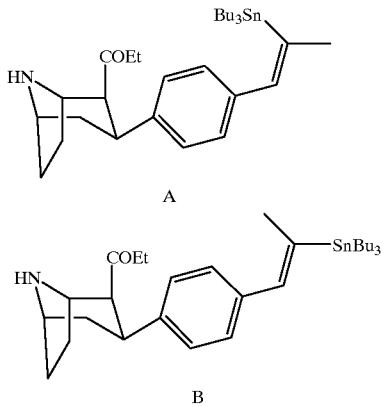

(Z) and (E)-2β-Propanoyl-3β-[4-(2-tributylstannylpropenyl)phenyl]-8-azabicyclo[3.2.1]octane.

Tropane (126 mg, 0.45 mmol) was dissolved in benzene (5 mL) and AIBN (20 mg, 0.12 mmol) was added. The mixture was lowered into an oil bath set at 90° C. Bu$_3$SnH (0.24 mL, 0.90 mmol) was added in one portion. Refluxing was continued for 4 h. More AIBN (10 mg, 0.06 mmol) and Bu$_3$SnH (0.12 mL, 0.45 mmol) were added. Refluxing was continued overnight. The solvents were removed and chromatography of the residue over silica chromatography using 5% Et$_3$N/ether gave A (16.5 mg, 23%): [α]$^{25}$D=−69.2° (c0.8); FTIR (neat) 2954, 2923, 1700, 1463, 1406 cm$^{-1}$; $^1$H NMR (CDCl$_3$) δ 7.17 (d, 1 H, J=1.5 Hz), 7.05 (b s, 4 H), 3.69 (m, 1 H), 3.57 (br d, 1 H, J=6.2 Hz), 3.18 (ddd, 1 H, J=14.5, 5.4, 5.4 Hz), 2.89 (br d, 1 H, J=5.4 Hz), 2.42 (ddd, 1 H, J=14.5, 14.5, 2.5 Hz), 2.54–1.95 (m, 3 H), 2.07 (d, 3 H, J=1.5 Hz), 1.78–1.15 (m, 16 H), 0.91–0.60 (m, 18 H); $^{13}$C NMR (75.45 MHz, CDCl$_3$) δ 215.0, 144.1, 140.7, 140.5, 139.5, 127.6, 127.3, 56.2, 55.7, 53.5, 38.8, 36.4, 33.9, 29.0, 28.1, 27.5, 27.3, 13.6, 10.5, 7.0; Anal. Calcd for C$_{31}$H$_{51}$NOSn: C, 65.04; H, 8.98; N, 2.45. Found: C, 65.06, H, 9.03; N, 2.43. B (106 mg, 42%): [α]$^{25}$D=−66.5° (c0.8, CHCl$_3$); FTIR (neat) 2953, 2923, 2870, 1700, 1458, 1408 cm$^{-1}$; $^1$H NMR (CDCl$_3$) δ 7.17 (d, 2 H, J=8.4 Hz), 7.10 (d, 2 H, J=8.4 Hz), 6.52 (d, 1 H, J=1.5 Hz), 3.71 (m, 1 H), 3.57 (br d, 1 H, J=6.2 Hz), 3.22 (ddd, 1 H, J=13.2, 5.1, 5.1 Hz), 2.90 (br d, 1 H, J=5.9 Hz), 2.43 (ddd, 1 H, J=13.2, 3.2, 2.6 Hz), 2.24–1.95 (m, 3 H), 2.07 (d, 3 H, J=1.5 Hz), 1.78–1.21 (m, 16 H), 0.95–0.80 (m, 15 H), 0.69 t, 3 H, J=7.9 Hz); $^{13}$C NMR (75.45 MHz, CDCl$_3$) δ 215.2, 143.8, 140.2, 138.5, 136.4, 128.9, 127.2, 56.3, 55.8, 53.5, 38.8, 36.3, 33.8, 29.2, 29.1, 27.6, 27.3, 21.1, 13.7, 9.2, 6.9; Anal. Calcd for C$_{31}$H$_{51}$NOSn: C, 55.04; H, 8.98, N, 2.45. Found: C, 64.99, H, 8.96; N, 2.53.

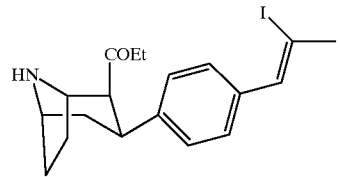

(Z)-2β-Propanoyl-3β-[4-(2-iodopropenyl)phenyl]-8-azabicyclo[3.2.1]octane.

The vinyltin tropane (40 mg, 0.070 mmol) was dissolved in CH$_2$Cl$_2$(5 mL) and argon was passed through for 10 min. Iodine (107 mg, 0.42 mmol) was added and the mixture was stirred at room temperature overnight. Aqueous Na$_2$S$_2$O$_3$ solution was then added, followed by NH$_4$OH. The mixture was saturated with solid NaCl and extracted with CH$_2$Cl$_2$ (5×20). The combined organic extracts were dried (MgSO$_4$) and evaporated. Chromatography of the residue over silica using 5–15% Et$_3$N/ether gave iodonated tropane (16.2 mg, 57%): [α]$^{25}$D=−97.3° (c 0.3, CHCl$_3$); FTIR (neat) 2937, 2911, 1694, 1406 cm$^{-1}$; $^1$H NMR (CDCl$_3$) δ 7.34 (d, 2 H, J=8.1 Hz), 7.12 (d, 2H, J=8.1 Hz), 6.60 (s, 1 H), 3.73 (m, 1 H), 3.59 (br d, 1 H, J=5.1 Hz), 3.25 (ddd, 1 H, J=15, 5.5, 5.5 Hz), 2.90 (br d, 1 H, J=5.5 Hz), 2.69 (s, 3 H), 2.45 (ddd, 1 H, J=15, 15, 2.2 Hz), 2.22–1.95 (m, 3 H), 1.78–1.55 (m, 4 H), 0.68 (t, 3 H, J=7.3 Hz); $^{13}$C NMR (75.45 MHz, CDCl$_3$) δ 215.2, 141.6, 136.8, 134.3, 128.6, 127.2, 100.0, 56.1, 55.7, 53.4, 38.9, 36.4, 35.3, 33.5, 29.0, 27.5, 7.0; Anal. Calcd for C$_{19}$H$_{24}$NOI: C, 55.75; H, 5.91; N, 3.42. Found: C, 55.97; H, 6.00; N, 3.25.

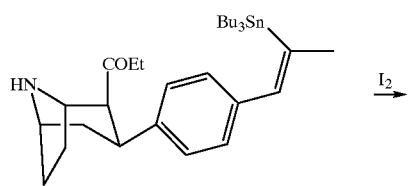
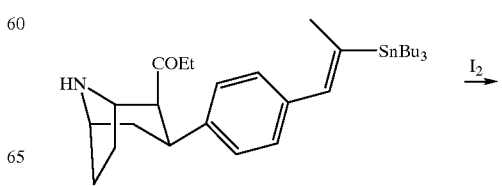

-continued

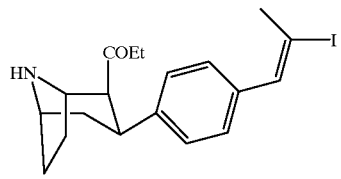

(E)-2β-Propanoyl-3β-[4-(2-iodopropenyl)phenyl]-8-azabicyclo[3.2.1]octane.

The vinyltin tropane (53.6 mg, 0.094 mmol) was dissolved in $CH_2Cl_2$ (7 mL) and argon was passed through for 10 min. Iodine (143 mg, 0.56 mmol) was added and the mixture was stirred at room temperature overnight. Aqueous $Na_2S_2O_3$ solution was then added followed by $NH_4OH$. The mixture was saturated with solid NaCl and extracted with $CH_2Cl_2$ (5×20). The combined organic extracts were dried ($MgSO_4$) and evaporated. Chromatography of the residue over silica using 5–15% $Et_3N$/ether gave iodinated tropane (28.9 mg, 75%): $[\alpha]^{25}D = -77.1°$ (c 0.28, $CHCl_3$); FTIR (neat) 2938, 2913, 1700, 1406 $cm^{-1}$; $^1H$ NMR ($CDCl_3$) δ 7.20 (d, 1 H, J=1.1 Hz), 7.11 (s, 4 H), 3.73 (m, 1 H), 3.59 (br d, 1 H, J=5.5 Hz), 3.20 (ddd, 1 H, J=14.2, 5.1, 5.1 Hz), 2.90 (br d, 1 H, J=5.1 Hz), 2.58 (d, 3 H, J=1.1 Hz), 2.41 (ddd, 1 H, J=14.2, 2.6, 2.6 Hz), 2.2–1.96 (m, 3 H), 1.76–1.50 (m, 4 H), 0.67 (t, 3 H, J=7.3 Hz); $^{13}C$ NMR (75.45 MHz, $CDCl_3$) δ 214.8, 141.5, 140.4, 135.6, 128.2, 7.5, 98.1, 56.2, 55.7, 53.4, 38.6, 36.3, 33.6, 29.3, 29.1, 27.6, 6.9; Anal. Calcd for $C_{19}H_{24}NOI$: C, 55.75; H, 5.91; N, 3.42. Found: C, 55.95; H, 6.00; N, 3.35.

What is claimed is:

1. A 3-aryltropane compound having the formula:

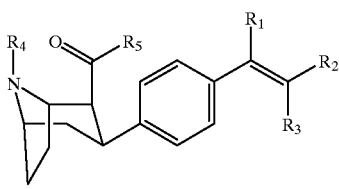

$R_1$ is selected from the group consisting of hydrogen and $C_1$ to $C_8$ alkyl;

$R_2$ is selected from the group consisting of hydrogen, iodo, radioisotopic halo, $C_1$ to $C_8$ alkyl and tri lower alkyl ($C_1$ to C8) tin; and $R_1$ and $R_2$ may be fused by a —N(Me)CH=CH— to form a pyrrole ring;

$R_3$ is selected from the group consisting of hydrogen, iodo, radioisotopic halo, or $C_1$ to $C_8$ alkyl;

$R_4$ is selected from the group consisting of hydrogen and $C_1$ to $C_8$ alkyl; and, $R_5$ is selected from the group consisting of hydrogen or $C_1$ to $C_8$ alkyl, and salts, solvates and hydrates thereof;

and further providing that one of $R_2$ and $R_3$ is a radioisotopic halo.

2. A 3-aryltropane compound having the formula:

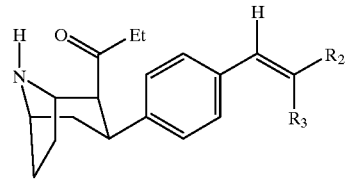

wherein Et is ethyl; and wherein one of $R_2$ and $R_3$ is radioisotopic iodo and the other is selected from the group consisting of hydrogen and $C_1$ to $C_8$ alkyl.

3. A 3-aryltropane compound of claim 2 wherein Et is ethyl; $R_2$ is radioisotopic iodo, and $R_3$ is hydrogen.

4. A 3-aryltropane compound of claim 2 wherein Et is ethyl; $R_2$ is radioisotopic iodo; and $R_3$ is methyl.

5. A 3-aryltropane compound of claim 2 wherein Et is ethyl; $R_2$ is methyl; and $R_3$ is radioisotopic iodo.

6. A 3-aryltropane compound having the formula:

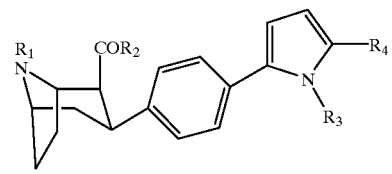

wherein $R_1$ is selected from the group consisting of hydrogen and $C_1$ to $C_8$ alkyl;

$R_2$ is selected from the group consisting of hydrogen and $C_1$ to $C_8$ alkyl;

$R_3$ is selected from the group consisting of hydrogen and $C_1$ to $C_8$ alkyl; and $R_4$ is selected from the group consisting of hydrogen and $C_1$ to $C_8$ alkyl.

7. A compound according to claim 1 wherein $R^2$ and $R^3$ are independently selected from H, $^{123}I$, $^{125}I$, $^{131}I$, $^{18}F$, tributyltin, trimethyltin and methoxy, $C_1$ to $C_8$ alkyl.

8. A compound according to claim 1, wherein $R^2$ and $R^3$ are independently selected from H, I, Br, $^{123}I$ and trimethyltin.

9. A compound according to claim 1 wherein one of $R^2$ and $R^3$ is $^{123}I$.

10. A radiopharmaceutical composition, comprising a radiopharmaceutically acceptable carrier and a compound as defined in claim 1 in an amount effective to image a human brain.

11. A radiopharmaceutical composition comprising a radiopharmaceutically acceptable carrier and a compound as defined in claim 9 in an amount effective to image a human brain.

12. A method of radioimaging a human brain comprising the step of administering systemically to a patient a radiopharmaceutical composition as defined in claim 10, allowing the radiopharmaceutical to localize within the brain, and then taking an image of the brain of the patient so treated.

13. A method of radioimaging a human brain comprising the step of administering systemically to a patient a radiopharmaceutical composition as defined in claim 11, allowing the radiopharmaceutical to localize within the brain, and then taking an image of the brain of the patient so treated.

14. A pharmaceutical composition comprising a pharmaceutically acceptable carrier and, in an amount effective to antagonize 5-HT receptor stimulation, a compound of Formula (1):

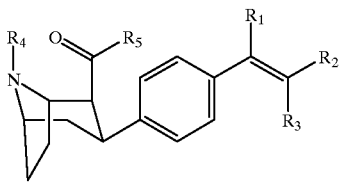

wherein $R_1$ is selected from the group consisting of hydrogen and $C_1$ to $C_8$ alkyl;

$R_2$ is selected from the group consisting of hydrogen, iodo, radioisotopic halo, $C_1$ to $C_8$ alkyl and tri lower alkyl ($C_1$ to $C_8$) tin; and $R_1$ and $R_2$ may be fused by a —N(Me)CH=CH— to form a pyrrole ring;

$R_3$ is selected from the group consisting of hydrogen, iodo, radioisotopic halo, or $C_1$ to $C_8$ alkyl;

$R_4$ is selected from the group consisting of hydrogen and $C_1$ to $C_8$ alkyl; and, $R_5$ is selected from the group consisting of hydrogen or $C_1$ to $C_8$ alkyl, and salts, solvates and hydrates thereof;

and further providing that one of $R_2$ and $R_3$ is a radioisotopic halo.

15. A pharmaceutical composition comprising a pharmaceutically acceptable carrier and in an amount effective to bind to the reuptake site, a compound as defined in claim 3.

16. A method for treating a patient having a medical condition for which a 5-HT receptor antagonist is indicated, comprising the step of administering to the patient a pharmaceutical composition as defined in claim 14.

17. A method for treating a patient according to claim 16, wherein the medical condition is depression.

18. A method for treating a patient according to claim 16, wherein the medical condition is attention deficit disorder.

19. A method for treating a patient according to claim 16, wherein the medical condition is obesity.

20. A method for treating a patient according to claim 16, wherein the medical condition is cocaine addiction.

21. A 3-aryltropane compound having the formula:

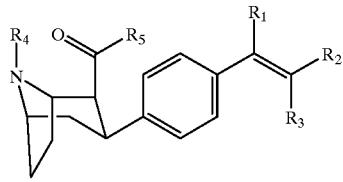

whereby $R_1$ and $R_2$ are fused by a —N(Me)CH=CH— to form a pyrrole ring;

$R_3$ is selected from the group consisting of hydrogen, iodo, or $C_1$ to $C_8$ alkyl;

$R_4$ is selected from the group consisting of hydrogen and $C_1$ to $C_8$ alkyl; and, $R_5$ is selected from the group consisting of hydrogen or $C_1$ to $C_8$ alkyl, and salts, solvates and hydrates thereof.

* * * * *